United States Patent [19]

Früngel et al.

[11] 4,178,512

[45] Dec. 11, 1979

[54] DEEPWATER IN-SITU FLUOROMETER

[75] Inventors: Frank Früngel, Hamburg; Eberhard Gelbke, Uetersen, both of Fed. Rep. of Germany

[73] Assignee: Impulsphysik GmbH, Hamburg, Fed. Rep. of Germany

[21] Appl. No.: 926,847

[22] Filed: Jul. 21, 1978

[51] Int. Cl.$^2$ .................... G01N 21/38; G01V 5/00
[52] U.S. Cl. .................... 250/461 R; 250/253
[58] Field of Search ............... 250/253, 354, 355, 365, 250/372, 373, 461 R, 461 B

[56] References Cited

U.S. PATENT DOCUMENTS

| | | | |
|---|---|---|---|
| 3,497,690 | 2/1970 | Wheeless, Jr. et al. | 250/461 B |
| 3,501,639 | 3/1970 | Monroe | 250/461 R |
| 3,666,945 | 5/1972 | Früngel et al. | 250/365 |
| 3,942,003 | 2/1976 | Apenberg et al. | 250/253 |

*Primary Examiner*—Alfred E. Smith
*Assistant Examiner*—Janice A. Howell
*Attorney, Agent, or Firm*—Michael J. Striker

[57] ABSTRACT

An onboard power supply and metering unit is connected, via an overboard cable e.g., 1000 meters long, to an underwater light-pulse projecting unit and a fluoroescence-sensing receiver unit. The operating power is transmitted to the underwater units by an onboard constant-current source, instead of a voltage source. Likewise, the output signal of the receiver unit is transmitted through the cable in the form of a current, not a voltage. The current of the receiver's photodiode is integrated, the peak value of the integral determined and held, this held value logarithmized, the logarithmized value sampled and held, and the held voltage converted to a current constituting the output signal. The offset of the peak detector and the input stage of the log amplifier are balanced automatically, by a balancing signal applied during pulse measurements, but derived between pulse measurements. The balancing signal is derived by integrating a signal derived from the log amplifier's output signal, and is applied to the input of the peak detector, with the peak detector converted to simple voltage-follower operation during the deriving of the balancing signal.

6 Claims, 7 Drawing Figures

DEEPWATER IN-SITU FLUOROMETER

BACKGROUND OF THE INVENTION

The present invention relates to in-situ fluorometers of the type adapted for underwater use, and especially deep underwater use, and constitutes an improvement relative to, for example, the fluorometer disclosed in commonly owned U.S. Pat. No. 3,666,945 of Frank Früngel et al.

The basic principle of operation of deepsea in-situ fluorometers is relatively simple. The fluorometer has a power supply and various meters, and the like, provided onboard a vessel. A cable, having a length for example on the order of 1000 meters, is connected to the power supply and meters, and hangs down overboard, with the fluorometer's measuring equipment connected at its other end, e.g., 1000 meters below the surface, the fluorometer sometimes being towed. Fluorometers of the type in question can alternatively be used in less deep rivers and bodies of water, i.e., despite their heavy-duty deepsea construction.

The underwater equipment includes a light transmitter and a light receiver. Pulses of light emitted from the transmitter are used to excite fluorescent substances in the water being investigated, e.g., bioplasma already present in the water and being investigated to ascertain water composition, or fluorescent tracer elements added to the water for example when investigating the movement or flow of water within a body of water. The emitted radiation excites the fluorescent material. The fluorescent radiation is detected by the receiver and converted into an electrical signal, which is then amplified and/or otherwise processed and transmitted along the length of the long cable to onboard the vessel, where the signals are fed into meters, or the like, for read-out.

Although the basic operating principle is simple, practical problems with such in-situ fluoremeters are so enormous as to greatly affect operativeness itself.

Thus, for example, it is conventional practice to utilize for the onboard power supply a stabilized voltage source. However, the resistance of the e.g., 1000-meter cable connecting the voltage source to the underwater equipment is quite substantial, requiring the provision of a matching resistance, to assure that the voltage actually fed to the underwater equipment is of sufficiently large magnitude. This is inherently power-consumptive. Even if the power supply itself is voltage-stabilized, it is also necessary that the voltage received by the underwater equipment be stabilized, for the obvious reason of measuring accuracy. If different lengths of connecting cable are employed, for different depth ranges to be explored, this will either have to be taken into account by corresponding adjustment of the underwater equipment and/or will involve further power waste. Despite all this, it has been found in practice that fluctuations in the voltage supplied to the underwater equipment are simply unavoidable. If the voltage magnitude employed is to be kept reasonably low, such fluctuations can seriously detract from measuring accuracy.

A further problem relates to the conflicting requirements of high sensitivity and immunity to the effect of daylight penetrating below water. In the past, the photosensitive element of the underwater receiver was typically a photomultiplier, to take advantage of the high photosignal strengths which such elements could achieve. However, if underwater daylight impinged on such photomultipliers, a corresponding D.C. current component was generated exhibiting the same high gain as the actual pulsed light signal of interest, e.g., a gain factor of $10^6$. This resulted in very severe electronic noise and also in thermal overloading of the photomultipliers. Accordingly, it was necessary, in such earlier fluorometers, either to work in darkness or else somehow shield the photomultiplier from underwater light, by relatively complicated means. For that reason, commonly owned U.S. Pat. No. 3,666,945 proposed replacement of the photomultiplier with a simple silicon semiconductor photodiode. Although photodiodes do not exhibit the high gain of photomultipliers, their quantum efficiency per se is higher than the primary efficiency of a photomultiplier. This made it possible to avoid the enormous problems of exposure to underwater light, while still generating a signal of sufficient strength for processing.

This improvement, however, was not without problems. Exposure of a simple photodiode to underwater light also results in the generation of a great amount of singal noise, which may indeed be quite violent and energetic. Furthermore, this noise does not just consist of a steady D.C. component corresponding to steady underwater illumination; such a component can be suppressed, more or less, using high-frequency filtering. Rather, the noise generated is to a great extent high-frequency noise resulting from electronic excitation mechanisms internal to the structure of the photodiode element, and this noise cannot be suppressed by merely using high-frequency filters. This high-frequency noise forms a background for the signal of interest, and therefore the signal of interest must somehow be made sufficiently strong to be distinguished from its background. For example, when investigating water movements using fluorescent tracers, the requisite boost in the level of the signal of interest is achieved by increasing the amount of fluorescent tracer employed. However, fluorescent tracers are quite expensive. For example, the investigation of the movement of a large body of water, e.g., the Gulf Stream, requires many hundreds of runs, and the amount of tracer needed for each run may cost on the order of $100. The cost of the tracer, accordingly, can in the long run dwarf the cost of all the equipment itself. If, for example, the sensitivity of the receiver could be increased by 3—i.e., if one could use $\frac{1}{3}$ the normal amount of tracer to achieve the same signal strength relative to its background noise—this would already signify a very great cost saving.

A problem which, as will become clearer below, is interconnected with sensitivity is the manner in which the signal to be processed is formed. In the prior art, the peak value of the voltage produced by the photodiode is ascertained, and thereafter this peak-voltage value is used for signal processing. The prior-art peak-voltage technique has been adopted as a logical consequence of adopting a pulse technique. Pulse techniques have been adopted to perform intermittent, relatively high-energy measurements, and thereby enormously reduce power consumption, compared to what would be the case if, unthinkably, an uninterruptedly constant fluorescence-excitation technique were employed. Inasmuch as pulse techniques make possible the generation of high peak values, it has thus far seemed only natural to base the signal processing on the peak-voltage value produced by the receiver's photodiode. However, this can create serious practical difficulties with respect to accuracy.

When the light source used for the underwater transmitter unit of the apparatus is for example a flash discharge lamp, we have found that the quantity of light emitted per light pulse is quite invariable, if the transmitter is well enough designed. In contrast to the total light emitted per light pulse, however, the peak value of light emitted per light pulse has been found to be variable enough to detract from measuring accuracy. Thus, prior-art systems, basing their signal processing as they do on the detected peak-voltage value of the photodiode, are limited as to accuracy in correspondence to the variation in the peak-value of emitted light per pulse. Loss of accuracy is a disadvantage whose significance requires no explanation. However, a related disadvantage results from the peak-voltage technique of the prior art. In the type of fluorometers in question, the output signal transmitted via cable to the onboard equipment is logarithmic; i.e., the photodiode's peak-voltage, or an amplified voltage derived therefrom, is applied to the input of a log amplifier, and the log amplifier's output signal is transmitted to the onboard equipment. Unfortunately, with the type of signal-generation and-processing techniques traditional for such fluorometers, the linear range of the logarithmic transformation achieved is found to be limited to about three decades, and to be furthermore considerably less than ideal. Accordingly, the signal transmitted to the onboard equipment will often be imperfectly logarithmic and for that reason actually inaccurate; very complex techniques, e.g., involving computer analysis, may be required to correct the imperfectly logarithmic character of the signal received onboard, to convert it into a sufficiently accurate signal. Alternatively or in addition thereto, because of the limited number of decades through which near-ideal logarithmization can be implemented, it may be necessary to change the decades-range of the log amplifier, when the onboard personnel observe that the returned signal is of a value not corresponding to the decades-range at which the logarithmization can properly occur. This may require hoisting of the underwater apparatus onboard to readjust the log amplifier, or complex techniques such as remote-control adjustment of the log amplifier's range.

A still further problem with the type of insitu fluorometer in question relates to component stability. Even when the components of the underwater apparatus, and especially the receiver, are tested and selected with utmost care, e.g., integrated circuits selected in accordance with military specifications, instability in the null point of the measuring system has been unavoidable. Even highest-quality semiconductor elements exhibit only limited stability in the course of time, obviously due to internally occurring diffusion processes in silicon. Of course, lack of stability is always undesirable. However, in fluorometers of the type in question, the practical difficulties are already so numerous, interrelated and connected with operativeness and accuracy per se, that lack of null-point stability, particularly in combination with all the problems of sensitivity, accuracy, limited power consumption, and so forth, becomes disproportionately troublesome compared to many other types of measuring instruments.

The problems with prior-art fluorometers as discussed above, are very difficult to attack individually, because of their interrelated nature. Attempts to alleviate just one of these problems will typically worsen others, or bring other problems into existence. Likewise, a mere willingness to employ prior-art principles, but with no limits on the cost of the circuitry used to implement them, in the hope of avoiding the problems discussed above by means of ultra-high-quality components, and the like, are not per se sufficient, because these problems flirt with the limits of what is commercially available at any price. Furthermore, of course, unlimited cost is not actually acceptable.

SUMMARY OF THE INVENTION

Accordingly, it was the general object of the present invention to somehow come up with a new overall approach to the design of such in-situ fluorometers, such as to create a greater possibility for reducing the degree of the problems in question, i.e., without merely trying to increase the quality of the components utilized, the cost and quality of the prior-art circuit stages, and so forth.

If one had to broadly characterize the new approach adopted, one could call it a changeover from voltage-oriented operation to current- or charge-oriented operation. Of course, in the context of many types of measuring instruments, but especially in-situ fluorometers of the type here in question, there is a strong bias, in part unconscious and uncritical, to voltage-oriented operation. The combination of individual techniques constituting the present invention results from an initial attempt to somehow find a new and different basic approach, the approach decided upon being current- or charge-oriented operation. Once this basic approach had been adopted, and an attempt to change as much as possible from voltage-oriented principles to current-oriented principles began, it was found that this was indeed a fruitful approach, and that more and more of the problems in question were becoming amenable to improvement.

The changeover to current- or charge-oriented operation exists at several levels in the present invention. At the level of the onboard power supply, use is not made of the customary stabilized voltage source, but instead a constant-current source is employed. The underwater equipment is furnished with stabilized operating current, instead of stabilized operating voltage. As a result, the problems associated with the long length of the underwater cable, e.g., 1000 meters, and the problem associated with occasional changes in the length of cable employed with particular equipment, are reduced. For the low voltage-magnitudes which will be involved, the current transmitted to the underwater equipment from the onboard constant-current source will be very constant, irrespective of cable length which simply becomes uncritical.

At the level of the photodiode signal, the changeover to current- or change-oriented operation involves a departure from the peak-photodiode-voltage technique traditional for such in-situ underwater fluorometers. Instead of ascertaining the peak-voltage value of the photodiode's signal, and then basing the signal processing on such value, in the present invention the current flowing through the photodiode is integrated during a received light pulse, to form an accumulation of charge which, in effects, already constitutes an amplification, which could be referred to as a charge amplification. This brings about several improvements relative to the peak-voltage value technique traditional for such fluorometers. First, the integration or accumulation of the photodiode-current's charge builds up, at an early stage, a signal of fair strength, sufficient for processing. This is roughly equivalent to an increase in sensitivity. Additionally, however, there is an increase in accuracy. As explained earlier, it has been found that, while the quantity of light emitted per light pulse is quite constant in a well designed system, the peak value of emitted light per pulse cannot be kept from exhibiting variation. Thus, the charge-amplification technique used in the present invention first represents a changeover from reliance on the photodiode's voltage to its current, but second and furthermore represents a departure from in particular the peak-voltage value technique traditional in the prior art. Because the photodiode-current's charge is accumulated during the course of a received light pulse, the thusly built-up signal more accurately corresponds to the content of the light pulse than a signal dependent solely upon the peak value of the pulse.

Thus, there is the advantage of increased accuracy, and also an advantage equivalent to amplification, and referred to herein as charge amplification.

During reception of the light pulse by the photodiode, i.e., during the integration of the photodiode current, the integral signal is transmitted via a gated switch to a resettable peak detector, which registers the maximum value achieved by the integral signal. The signal-transmission switch connects the output of the photodiode-current integrator to the input of the peak detector for only a brief interval, coincident with the emission of a light pulse by the transmitter unit of the apparatus. By thusly gating the peak detector, the peak detector is kept immune from white noise during the interpulse intervals. This, in combination with the charge-integration technique referred to above, has been found to per se raise, by a factor of about 3, the sensitivity of the receiver (to be distinguished from mere gain, which would apply to background noise as well as to the signal of interest). As explained earlier, such an increase in sensitivity is of enormous importance in terms of economy when fluorescent tracers are being employed.

The peak value of the photodiode-current integral signal registered by the peak detector, is then persistently applied to the input of a log amplifier, for a time interval sufficiently long for the log amplifier to fully respond, and thereby produce a corresponding logarithmized signal of the maximum accuracy of which it is capable. The application of a held signal, i.e., held by the aforementioned peak detector, thus serves to make possible the use of a log amplifier with a large dynamic range. It will be understood that, in the design of log amplifiers, there is typically a tradeoff between dynamic range and speed of response. Thus, in the present invention, the log amplifier receives the held maximum value of the integral of the photodiode current. This is in contrast, for example, to simply applying a straightforward photodiode voltage to the input of a log amplifier and transmitting the log amplifier's output signal. The technique of the present invention has been found in practice to result in a high-accuracy dynamic range of 1:10,000. Indeed, the accuracy is so high that the linear-versus-logarithmic relationship implemented is indistinguishable from ideal. If one were willing to tolerate the less-than-ideal logarithmization tolerated in the prior art, then one could push still higher the dynamic range resulting from the inventive logarithmization of the held peak value of integrated photodiode current, i.e., compared to what can be achieved with conventional prior-art logarithmization of photodiode voltage.

The logarithmized integrated-photodiode-current signal is then applied to a sample-and-hold-circuit, which holds the thusly determined value intermediate pulse measuring operations. The thusly held logarithmized signal is applied to an adapting stage, which has been preset to a range and gain such as to cause the ultimate output signal to vary within the desired range. After the logarithmized signal, at this point in the form of a voltage, has passed through the adapting stage, it is applied to a voltage-to-current convertor, and converted into a current, constituting the output signal of the underwater equipment. This output signal, in the form of a current not a voltage, is then transmitted through the underwater cable up to the meters onboard the vessel above. Again, because the output signal is being transmitted back to the vessel as a current, not a voltage, the length of the underwater cable ceases to be critical or even relevant for onboard signal evaluation.

Finally, after all the signal-processing work for one pulse measurement has been performed, and prior to the start of the next pulse measurement, an automatic offset drift control circuit is switched in. The output signal of the log amplifier is fed back through an integrator to the input of the resettable peak detector, which is now switched over from peak-detection operation to simple voltage-follower operation, and through the peak detector applied to the input of the log amplifier. As a result, offset drifts of the peak detector and input stage of the log amplifier are eliminated for the next pulse measurement.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
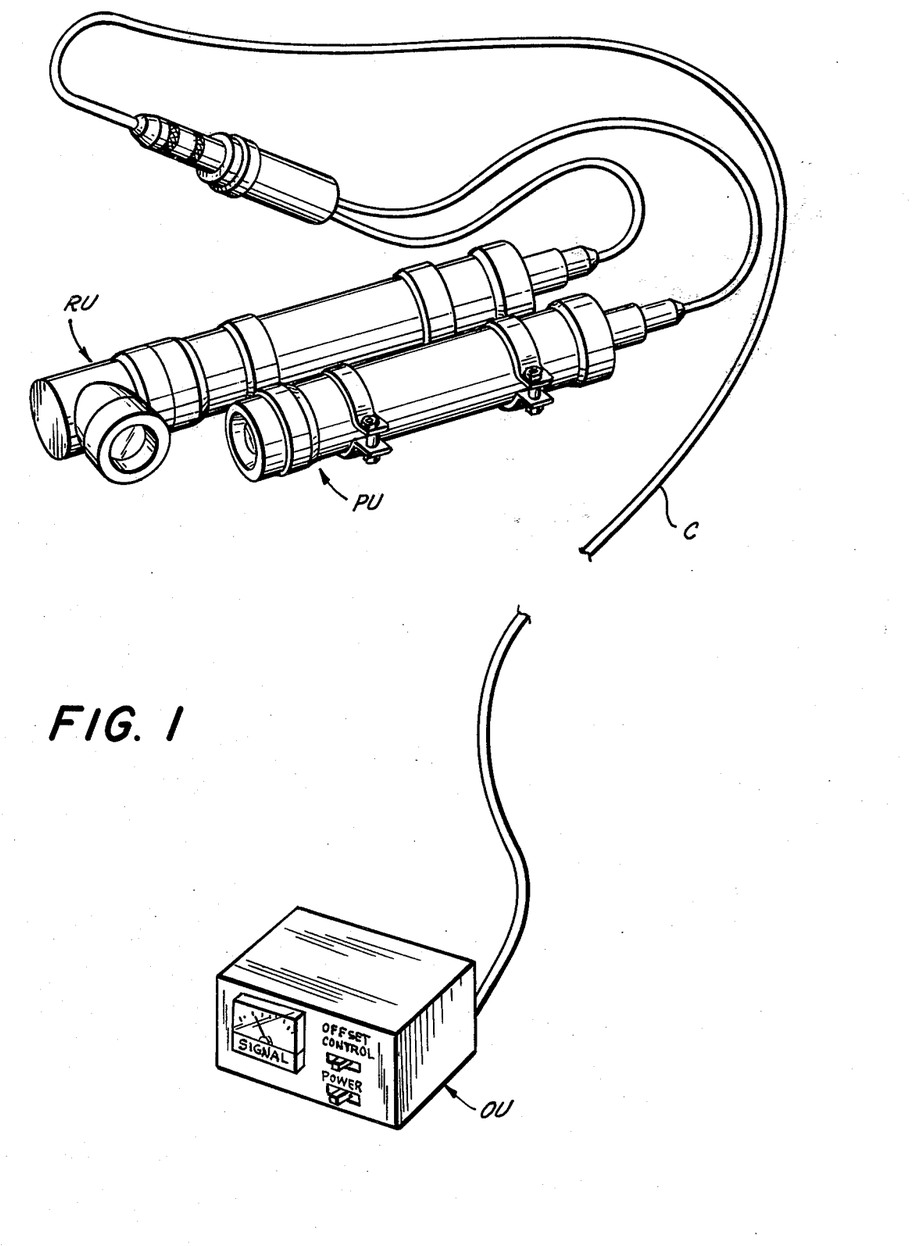
FIG. 1 is an overall view of an exemplary fluorometer in accordance with the invention.

FIG. 1 is an overall view of the inventive underwater in-situ fluorometer. The underwater equipment is essentially comprised of a projector unit PU which emits pulsed radiation for the purpose of fluorescence excitation, and a receiver unit RU which receives the fluorescent radiation emitted by the excited fluorescent material in the water, whether bioplasma or other material already present in the water or fluorescent tracers dumped into the water. The underwater equipment is connected by an overboard cable C, which may have a length on the order of 1000 meters, to an onboard unit OU. Onboard unit OU comprises a constant-current power supply pack, a meter on which the signal received from the underwater equipment is displayed, a power switch and an offset control switch used for zero checking.

Figure 2:
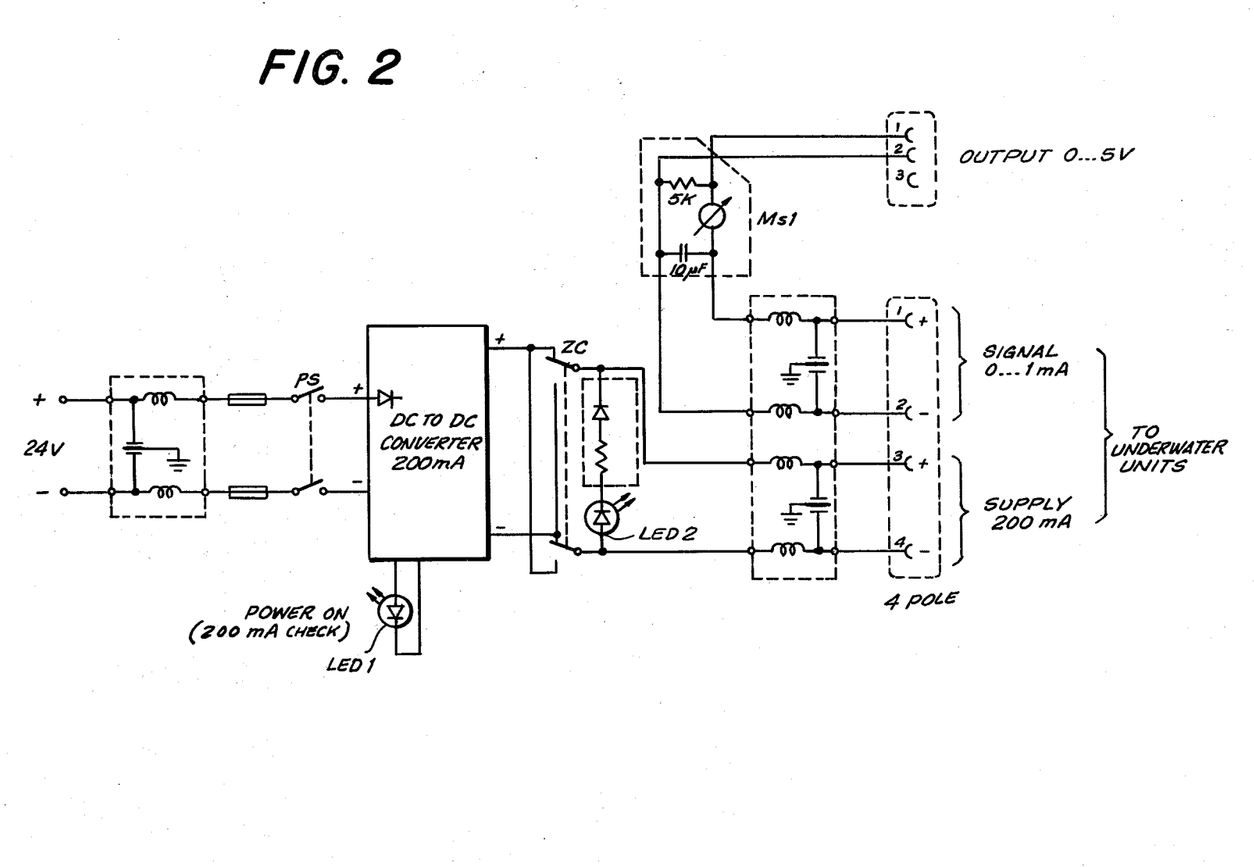
FIG. 2 depicts the internal circuitry of the onboard power supply and metering unit of the fluorometer.

FIG. 2 depicts the internal circuitry of the onboard unit OU. The onboard unit OU is connected as shown to a 24 V battery. The battery voltage is applied, via a noise filter, two safety fuses, and a double-pole power switch PS, to the input of a DC-DC converter. A diode circuit at the input of the DC-DC converter protects the converter from accidental wrong battery-voltage application. The output of the converter is a constant current of 200 mA for a maximum loop voltage of 45 V. When the power switch PS is closed and the converter operating properly, a first LED1 lights up, indicating to onboard personnel that the constant-current source is operating properly. The output of the constant-current source is transmitted, via a double-pole zero-check switch ZC and a noise filter, to the third and fourth terminals of the illustrated 4-pole connector, for transmission of the 200-mA constant supply current through the cable C to the underwater units. The purpose of zero-check switch ZC is explained further below, but essentially it is used to reverse the polarity of the power supplied to the underwater units for a zero-check. When zero-check switch ZC is flipped to its non-illustrated setting, for a zero-check, LED2 lights up, to indicate that a zero-check is being performed.

The 4-pole connector, at its first and second terminals, receives the signal transmitted via cable C from the underwater receiver unit RU. This signal is a current, not a voltage, and has a range of 0 to 1 mA. The received signal is transmitted, via a noise filter, to a signal meter Ms1, on which the received signal is displayed. A 5K-shunt across meter Ms1 is connected across the first and second terminals of a 3-pole connector, and makes available an output voltage whose range is 0 to 5 V, which can for example be fed to a recorder, or the like.

It is to be emphasized that both the transmitted supply power and the received signal are currents, not voltages, i.e., the power supply is in the form of a constant-current source, and the received signal is transmitted through cable C from underwater as a current, making the length of cable C uncritical.

Figure 3:
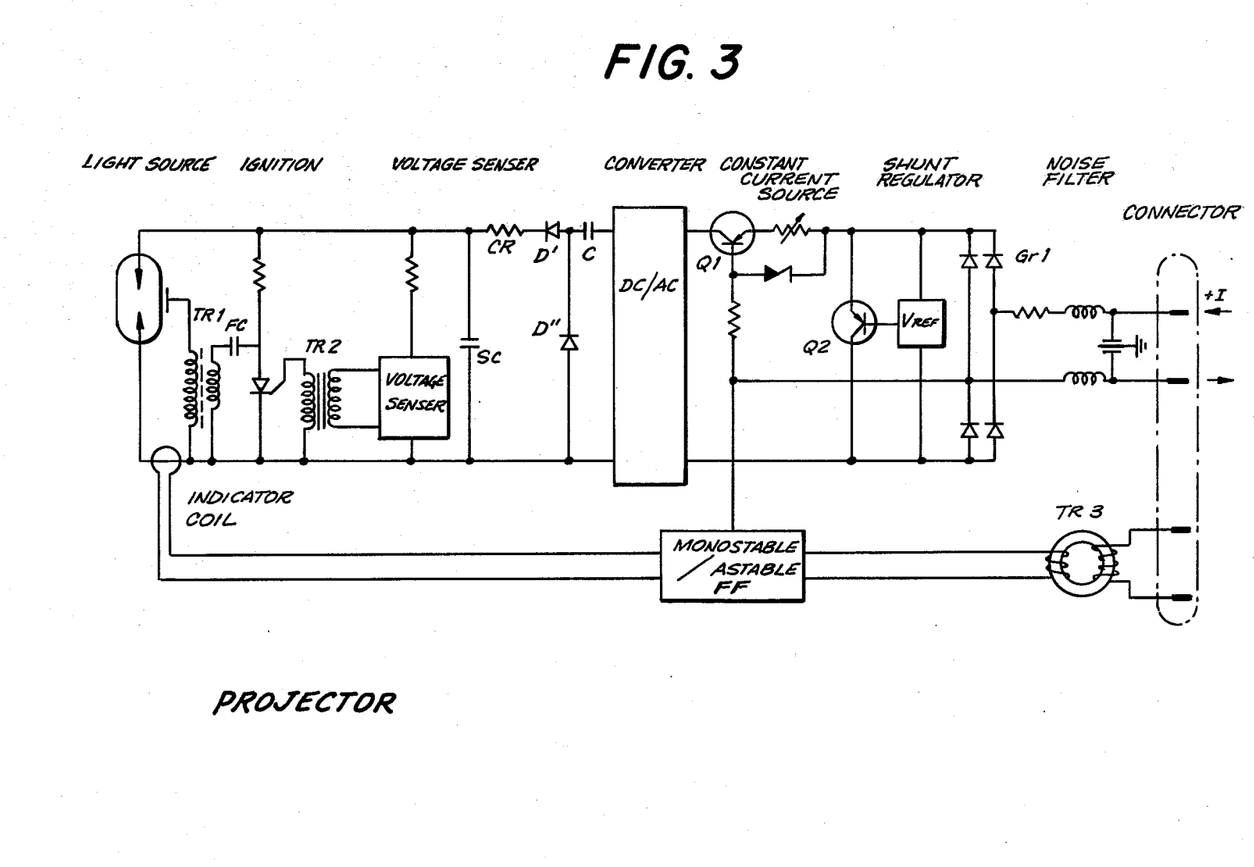
FIG. 3 depicts the internal circuitry of the underwater projector unit of the fluorometer.

FIG. 3 depicts the circuitry internal to the projector unit PU. At the right in FIG. 3, the constant 200-mA supply current I is received at the upper two terminals, and transmitted via a noise filter and a rectifier Gr1, to a shunt regulator. The shunt regulator comprises a reference-voltage unit $V_{ref}$ and a transistor Q2. A constant-current source, comprising a transistor Q1, an adjustable resistor, a zener diode, and a base resistor, supplies constant current to a DC-to-AC converter. The output voltage of the converter is doubled by a voltage-doubling stage C, D', D''. Via a charging resistor CR, the thusly doubled voltage is used to charge a storage capacitor SC. The voltage across storage capacitor SC is monitored by a voltage sensor, and when the voltage of SC has reached a predetermined value, the voltage sensor, via a transformer Tr2, fires an SCR, to discharge a firing capacitor FC through the primary of an ignition transformer Tr1. The voltage surge generated across the secondary of Tr1 is applied to the firing electrode of a flash-discharge light source, which produces an intense pulse of light. Immediately after this discharge, the storage capacitor SC charges back to its rated value, this taking about 100 ms, and another such high-intensity light pulse is emitted. The light-pulse repetition rate is accordingly 10 Hz. The flash-lamp discharge current is sensed by an indicator coil, which triggers a monostable flip-flop. The output signal of the monostable flip-flop is applied to a transformer Tr3, whose output signal is used as a gating signal for the receiver unit RU; the use of the gating signal is described further below.

During normal operation, the zero-check switch ZC is in the setting shown in FIG. 2, and the voltage polarity of the constant current I supplied to the input of the projector unit of FIG. 3 is as indicated. For a zero-check, switch ZC is shifted to its other setting, thereby reversing the polarity of the constant current supplied to the projector unit of FIG. 3. This polarity reversal renders non-conductive the constant-current-source transistor Q1, preventing the DC-AC converter from charging storage capacitor SC. The input current is also applied to a mode-control input of the flip-flop.

The flip-flop, in response to the polarity reversal of the supply, switches over from a monostable mode of operation to an astable or free-running mode, generating output pulses at a rate simulating normal operation. Accordingly, transformer Tr3 generates gating pulses simulating normal operation. These normal operation-simulating gating pulses are applied to the receiver unit RU, so that a zero check of the receiver unit without actual light pulses can be performed. The output signal must be zero, if no light pulse is emitted.

Figure 4A:
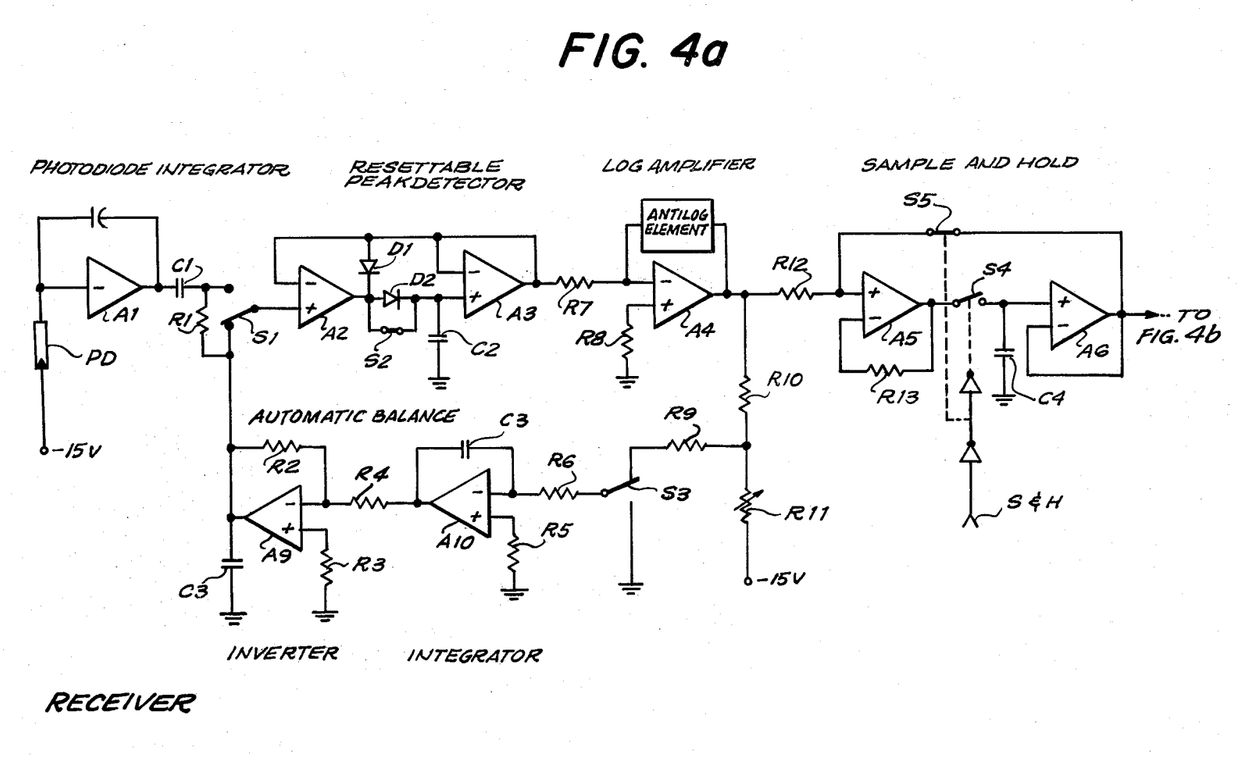
FIGS. 4a and 4b are respectively the left and right halves of a single diagram, depicting the internal circuitry of the underwater receiver unit of the fluorometer.
Figure 4B:
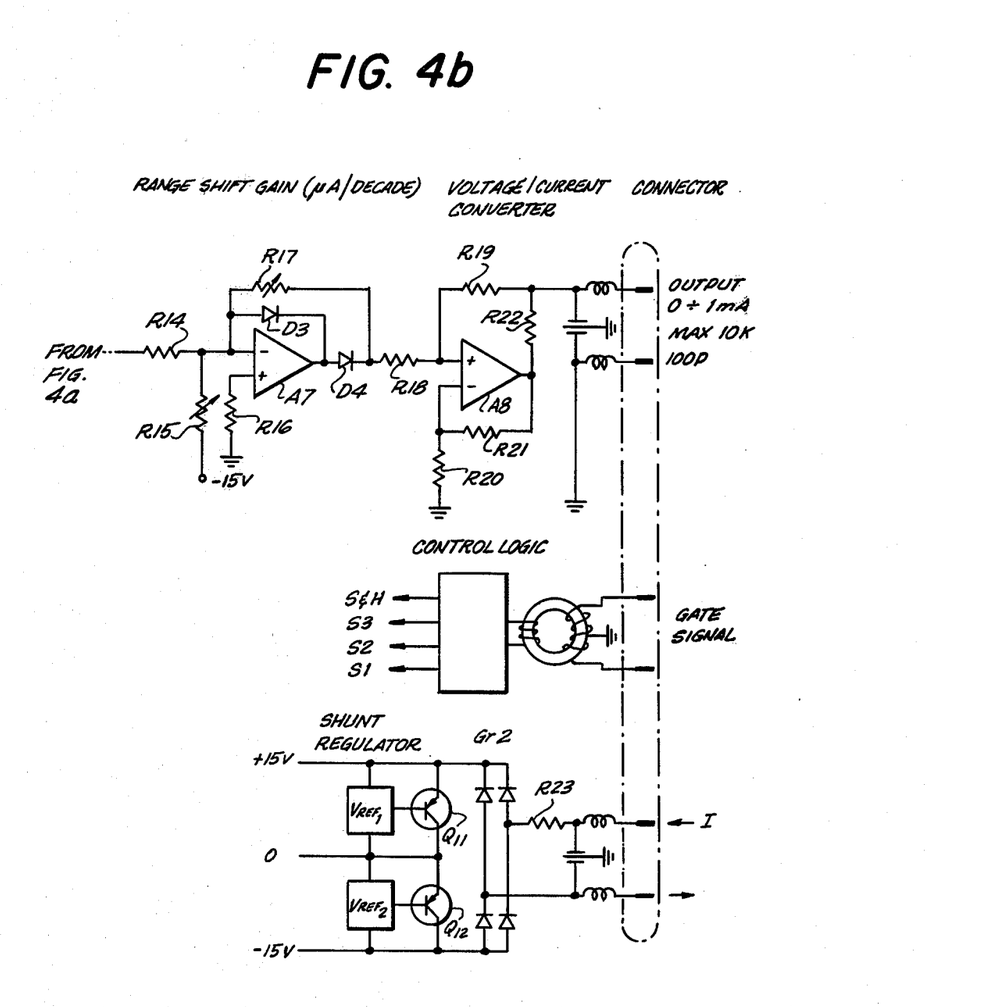

FIGS. 4a and 4b together constitute a diagram of the circuitry internal to the receiver unit RU. It is to be noted that, at the right in FIG. 4a, the output signal of op amp A6 is transmitted to the left terminal of resistor R14 in FIG. 4b.

Starting at the bottom right in FIG. 4b, it will be seen that the constant 200-mA supply current I is fed, via a noise filter, a resistor R23 and a rectifier Gr2, to a shunt regulator which comprises two transistors Q11, Q12, and two voltage-reference elements $V_{ref1}$, $V_{ref2}$. This shunt regulator supplies the +15 V, −15 V operating voltage for the remainder of the receiver-unit circuitry, and also establishes the 0 or ground voltage for the circuitry.

Further up in FIG. 4b, the gate signal is received from the output of the transformer Tr3 of the projector unit of FIG. 3, and is applied via a further transformer to the input of a control logic. The control logic is basically a timer, which generates four control signals S&H, S1, S2, S3, discussed further below.

Turning now to FIG. 4a, and starting at the left, PD denotes the silicon photodiode used as the light-receiving element of the receiver unit. The photodiode current is applied to an integrator. During pulse measurements, the integrated photodiode current is transmitted to a resettable peak detector. The held output signal of the latter is applied to a log amplifier. The output signal of the log amplifier is applied to a sample and hold stage. The signal held by the latter intermediate pulse measurements is transmitted (see FIG. 4b) to an adapting stage which is preset for range shift and gain, then converted to a current and transmitted as a current having a range of 0 to 1 mA up through cable C to the onboard unit OU.

The part of the receiver circuit shown in FIG. 4a is depicted in its stand-by condition, i.e., between pulse-measurement operations. In stand-by, the switches S1-S5 have the settings shown. With switch S2 of the resettable peak detector in its illustrated closed setting, the peak detector operates as a simple voltage follower. The voltage at the output of op amp A4 of the log amplifier is fed, via a voltage divider R10, R11, a resistor R9 and switch S3, to the input of an op-amp integrator A10, C3, R5, R6. The output voltage of this integrator is transmitted to an op-amp inverter A9, R2, C3, R3, R4. The inverted output voltage of the latter is transmitted, via switch S1, to the input of the peak detector. Because the charging diode D2 of the peak detector is short-circuited by the closed switch S2, the peak detector is presently operating as a simple voltage follower. The voltage at the output of op amp A2 is transmitted via op amp A3 to the inverting input of the log-amplifier's op amp A4. For a +4 V output voltage of op amp A4, the adjustable resistor R11 of the voltage divider R10, R11 is preset so that the voltage-divider tap be at zero voltage, and accordingly so that the input voltage to the integrator A10, C3, R5, R6 nominally be zero. In this way, offset and drift errors of the op amps A2, A3 and of the input circuitry of the log amplifier are eliminated, i.e., when after stand-by an actual pulse measurement begins and the switches S1-S3 assume their other settings.

When a light pulse is emitted by the projector unit of FIG. 3, a gating signal is produced at the output of transformer Tr3 of FIG. 3. This gating signal is applied (FIG. 4b) to the input of the control logic, which then generates control signals S&H, S1, S2, S3, for changing the settings of the switches S1, S2, S3 and the two switches S4, S5 of the sample and hold circuit of FIG. 4a. Of course, these switches can be electronic switches.

Figure 5:
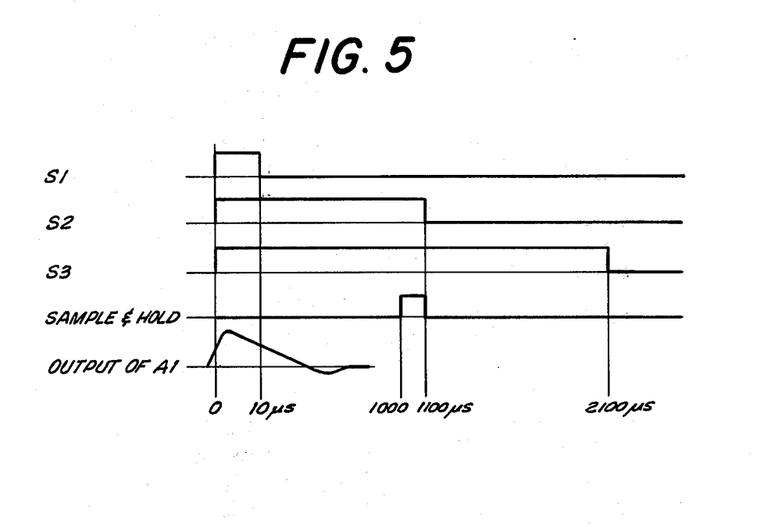
FIG. 5 is a timing diagram depicting the times of changes-of-setting of the switches within the receiver unit circuitry.

FIG. 5 depicts the timing and sequencing of the change of setting of switches S1-S5 and their return to stand-by setting, and also the output signal of the photodiode-current integrator A1. It will be noted that the switches S1-S3 all change to working setting simultaneously, whereas switches S4, S5 of the sample and hold circuit do not yet do so. The integrated photodiode-current signal at the output of amplifier A1 will be seen to increase fairly sharply and then begin to fall off somewhat more slowly, the peak value attained by the integrated photodiode-current signal occurring within the gating interval of gating switch S1.

The integrated photodiode-current signal at the output of amplifier A1 is applied, via gating switch S1, to the resettable peak detector A2, A3, C2, D1, D2. The peak value reached by the integrated photodiode-current signal is registered on capacitor C2, and is held by capacitor C2 for as long as switch S2 stays open. It will be seen from FIG. 5 that, although gating switch S1 stays open for only 10 microseconds, switch S2 stays open for an extra 1090 microseconds beyond that.

It will be noted that the last of all the switches to return to its stand-by setting is the switch S3. At the start of the pulse measurement, S3 assumes its lower setting, thereby disconnecting the input of integrator A10, C3, R5, R6, from the nominally zero voltage at the tap of voltage divider R10, R11 and instead connecting it to actual zero voltage. Accordingly, whatever output voltage had been achieved by op amp A9 at the end of the automatic null-point setting operation during the stand-by interval, remains constant at the output of op amp A9 during the pulse measurement.

The peak value of the integrated photodiode-current signal, now being held on peak-detector capacitor C2, is applied via the voltage-follower op amp A3 of the peak detector to the input of the log amplifier A4, R7, R8. The op amp A4 of the log amplifier is provided with an antilog element in its negative-feedback branch, in the ordinary way. As already indicated, the detected peak value of the integrated photodiode-current is held by C2, because S2 is open, for a time interval much longer than the S1 gating interval per se. Thus, the held peak value of the integrated photodiode-current signal can be applied to the log amplifier for a substantial time interval, giving the log amplifier all the time it needs to fully respond to the signal it is to logarithmize.

After the log amplifier has had all the time it needs to respond, and has produced at its output a logarithmized version of the integrated photodiode-current signal, only then, i.e., 990 microseconds after the 10-microsecond gating interval of gating switch S1 has ended, is the logarithmized signal sampled by the sample and hold circuit; i.e., only then do the switches S4, S5 assume their non-illustrated settings. S4 and S5 assume their non-illustrated settings for an interval of 100 microseconds duration, sufficient to assume that the logarithmized version of the integrated photodiode-current signal has been fully responded to, whereupon switches S4, S5 then return to their original settings, the sampled signal now being persistently held on holding capacitor C4.

Figure 6:
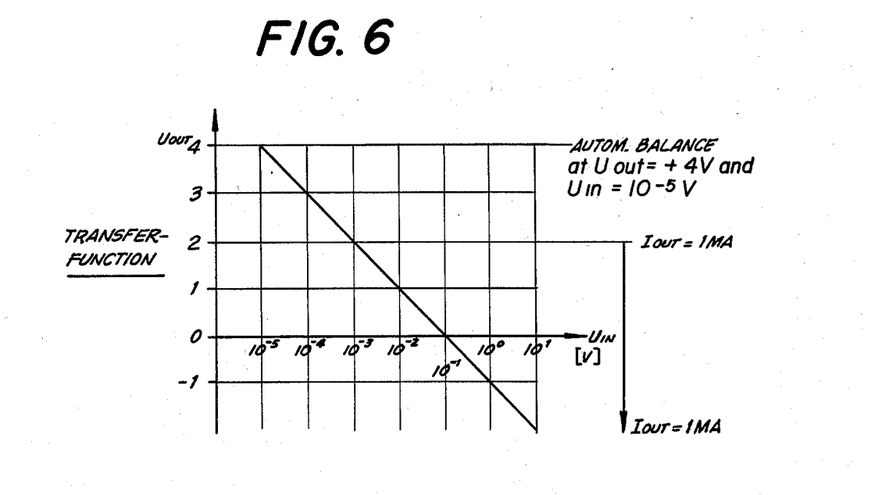
FIG. 6 depicts the transfer function of the receiver unit's circuit, as between the input of the logarithmizing means of the circuit and the output connection to the overboard cable.

The held, logarithmized version of the peak value of the integrated photodiode-current signal is transmitted through an adapting stage A7, R14-R17, D3, D4, to a voltage-to-current converter A8, R18-R22, which converts the logarithmized peak value of the integrated photodiode-current signal to the form of a signal current. This signal current is transmitted, through a noise filter, to the cable C, and fed in the form of a current up to the onboard unit OU. The gain and range shift of the adapting stage A7, R14-R17 is preset so that, for a range of four decades at the input of the log amplifier, the output signal current fed into cable C will have a range of 0-1 mA. This output current signal is independent of output loop resistance between 0 and 8 K. The transfer function, as between the input voltage to the log amplifier and the output current signal fed into the cable C, is depicted in FIG. 6.

It will be understood that each of the elements described above, or two or more together, may also find a useful application in other types of circuits and constructions differing from the types described above.

While the invention has been illustrated and described as embodied in a particular type of deep underwater in-situ fluorometer it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An improved in-situ fluorometer for underwater use, the fluorometer being of the type comprising an underwater projector unit operative for emitting pulses of fluorescence-exciting radiation, a cooperating underwater receiver unit operative for receiving the resultant fluorescent radiation and generating a meterable output signal, an onboard power supply and metering unit, and an overboard connecting cable electrically connecting the onboard power supply and metering unit to the underwater units for transmission of operating power to the underwater units and for transmission of the meterable output signal to the onboard power supply and metering unit,
  (a) the receiver unit comprising receiver circuit means, the projector unit comprising light-pulse-generating circuit means, the onboard power supply and metering unit comprising a constant-current source supplying operating power to the receiver circuit means and to the light-pulse-generating circuit means in the form of a constant current transmitted through said cable;
  (b) the onboard power supply and metering units comprising a meter, the receiver circuit means generating in response to detected fluorescent radiation an output signal in the form of a current and transmitting the output signal current to the meter through said cable,
  whereby, due to the energization of the circuit means to the underwater units by an onboard constant-current source, and due to the generation by the receiver unit of a cable-transmitted signal in the form of a current, the length of the overboard cable is made uncritical,
  (c) the receiver circuit means comprising:
  a photodiode exposed to the fluorescent radiation resulting from the pulsed radiation from the projector unit,
  integrating means integrating the photodiode current to form an integrated photodiode-current signal,
  peak-detecting means operative for determining and holding the peak value of the integrated photodiode-current signal, to form a held integrated photodiode-current peak-value persisting in time beyond the peak value of the integrated photodiode-current signal itself,
  gating means, connected to the signal-transmission path intermediate the photodiode and the peak-detecting means for permitting and preventing signal transmission,
  synchronizing means operative for rendering the gating means signal-transmissive for a brief time interval concurrent with the emission of a light pulse by the light-pulse-generating circuit means,
  logarithmic amplifier means receiving the held integrated photodiode-current peak-value signal and deriving therefrom a logarithmized integrated photodiode-current peak-value signal,
  sample-and-hold means operative for sampling and the holding the value of the logarithmized integrated photodiode-current peak-value signal, the sampling occurring subsequent to the signal-transmission interval of the gating means and subsequent to the peak-value determination by an interval sufficient to assure that the logarithmic amplifier means has fully responded to the held integrated photodiode-current peak-value signal, the signal held by the sample-and-hold means being in the form of a held voltage,
  voltage-to-current converting means receiving a voltage derived from that held by the sample-and-hold means and producing a corresponding current constituting the output signal transmitted from the receiver unit through said cable to the onboard meter,
  and automatic offset drift control means serving, during the time interval between the start of signal transmission by the gating means and the sampling by the sample-and-hold means, to counteract any offset and/or drift developed in the peak-detecting means and/or in the logarithmic amplifier means, by applying a balancing signal to the input of the peak-detecting means,
  this automatic offset drift control means comprising means operative, intermediate successive pulse-measurement operations, for deriving the balancing signal by feeding back to the input of the peak-detecting means a signal derived from the output signal of the logarithmic amplifier means.

2. A fluorometer as defined in claim 1, furthermore including adapting means connected between the output of the sample-and-hold means and the input of the voltage-to-current converting means, adjustable for varying the "gain" and "range shift" to which the voltage held by the sample-and-hold means is subjected.

3. A fluorometer as defined in claim 1, the gating means being connected between the output of the integrating means and the input of the peak-detecting means.

4. The fluorometer as defined in claim 3,
  the peak-detecting means including a voltage-holding capacitor, an input amplifier, and a charging rectifier charging the voltage-holding capacitor from the output of the input amplifier,
  the automatic offset drift control means including an integrator connected between the output of the logarithmic amplifier means and the input of the peak-detecting means, and furthermore including means short-circuiting the charging rectifier to thereby convert the peak-detecting means to simple voltage-follower operation during the deriving of the balancing signal.

5. The fluorometer as defined in claim 1, the meter on the onboard metering unit being a current meter.

6. The fluorometer as defined in claim 1, the meter of the onboard metering unit being a voltage meter.

* * * * *